United States Patent [19]

Pitt

[11] 4,271,325

[45] Jun. 2, 1981

[54] PROCESS FOR THE MANUFACTURE OF 1,1-DIHALO-4-METHYL-1,3-PENTADIENES

[75] Inventor: Harold M. Pitt, Lafayette, Calif.

[73] Assignee: Stauffer Chemical Company, Westport, Conn.

[21] Appl. No.: 867,866

[22] Filed: Jan. 9, 1978

Related U.S. Application Data

[63] Continuation of Ser. No. 742,801, Nov. 18, 1976, abandoned.

[51] Int. Cl.³ ............................................. C07C 21/19
[52] U.S. Cl. .................................................... 570/228
[58] Field of Search ..................... 260/654 D, 658 C; 570/228

[56] References Cited

U.S. PATENT DOCUMENTS

| | | | |
|---|---|---|---|
| 2,593,451 | 4/1952 | Hill et al. | 260/654 D |
| 2,803,680 | 8/1957 | Conrad | 260/654 D |
| 3,256,325 | 6/1966 | Wakasa et al. | 260/654 D |
| 3,299,152 | 1/1967 | Inaba et al. | 260/654 D |
| 4,053,380 | 10/1977 | Fiyita et al. | 260/654 D |
| 4,070,404 | 1/1978 | Lupichuck | 260/654 D |

FOREIGN PATENT DOCUMENTS 1023423 3/1966 United Kingdom ............... 260/658 C

*Primary Examiner*—Delbert E. Gantz
*Assistant Examiner*—Joseph A. Boska
*Attorney, Agent, or Firm*—M. Henry Heines

[57] ABSTRACT

The dehydrohalogenation of a 1,1,1,3-tetrahalo-4-methylpentane to a 1,1-dihalo-4-methyl-1,3-pentadiene is accomplished in the liquid phase in the presence of a catalytic amount of stannic chloride. The diene is a useful intermediate in the manufacture of insecticidal synthetic pyrethroid esters.

7 Claims, No Drawings

PROCESS FOR THE MANUFACTURE OF 1,1-DIHALO-4-METHYL-1,3-PENTADIENES

This is a continuation, of application Ser. No. 742,801, filed Nov. 18, 1976, now abandoned.

BACKGROUND OF THE INVENTION

Synthetic pyrethroid esters, similar in structure to naturally occurring pyrethrin, are well known as insecticides of high stability and low mammalian toxicity. These synthetic esters are superior to the pyrethrins found in nature in a number of ways. First, the naturally occurring pyrethrins are subject to very fast degradation and their insecticidal activity is neutralized by air and light. Second, the naturally occurring compounds are not available in great abundance and are costly to extract from their natural state. The synthesized variations of these compounds, on the other hand, have a higher stability, and yet are sufficiently degradable that they do not present environmental problems. They are also resistant to light induced oxidation. In addition, pyrethroids have a low toxicity for mammals and humans, relative to other insecticides, while exhibiting high insecticidal activity to a wide variety of insects.

One of the methods of preparation of these synthetic pyrethroids is disclosed in P. E. Burt, M. Elliott, A. W. Farnham, N. F. Janes, P. H. Needham, and D. A. Pullman, *Pesticide Science* 5, 791–799 (1974). According to this method, ethyldiazoacetate is reacted with 1,1-dichloro-4-methylpenta-1,3-diene to form ethyl(±)-cis, trans-2,2-dimethyl-3-(2,2-dichlorovinyl)-cyclopropanecarboxylate, which is then converted to the carboxylic acid. The latter was subsequently converted to the acid chloride, then reacted with 3-phenoxybenzyl alcohol in a Schotten-Baumann reaction, to produce 3-phenoxybenzyl 2,2-dimethyl-3-(2,2-dichlorovinyl)-cyclopropanecarboxylate, a well known insecticidally active pyrethroid ester. The above-mentioned diene can be prepared by the reaction of an appropriate sulfone with sodium hydroxide in a Ramberg-Bäckland type rearrangement. See L. Ramberg and B. Bäckland, *Arkiv. Kemi. Mineral. Geol.*, 13A, No. 27 (1940); also Bordwell and Cooper, *J. Am. Chem. Soc.*, 73, 5187–5190 (1951). The process involves a large number of steps, including those for the preparation of the sulfone, and requires the use of costly reagents.

The diene has also been prepared from chloral and isobutylene, Farkas, Kourim, and Sorm, *Collection Czechoslov. Chem. Commun.*, 24, 2230–2236 (1959), in a four-step process involving a costly zinc elimination.

A simpler process involves the addition of carbon tetrachloride to 3-methyl-1-butene to form 1,1,1,3-tetrachloro-4-methylpentane, followed by a liquid phase dehydrochlorination to form 1,1-dichloro-4-methyl-1,3-pentadiene. A variety of materials are known to catalyze this or similar liquid phase dehydrochlorinations, notably $BF_3$ and $FeCl_3$, see Topchiev, Bogomolova, and Gol'dfarb, *Doklady Akad. Nauk S.S.S.R.*, 107, 420–3 (1956), and Belgian Pat. No. 621,439. These known catalytic processes suffer from low yields due to polymerization of the product.

The object of this invention is to provide a novel process for the dehydrohalogenation of a 1,1,1,3-tetrahalo-4-methylpentane which entails polymerization to much less an extent than known processes, and thus produces higher yields of the desired product.

BRIEF DESCRIPTION OF THE INVENTION

This invention relates to a process for the manufacture of 1,1-dihalo-4-methyl-1,3-pentadiene which comprises contacting a 1,1,1,3-tetrahalo-4-methylpentane with a catalytic amount of stannic chloride, and recovering the product therefrom.

DETAILED DESCRIPTION OF THE INVENTION

In the process of the present invention, liquid stannic chloride, $SnCl_4$, is used as a cracking catalyst in the following reaction:

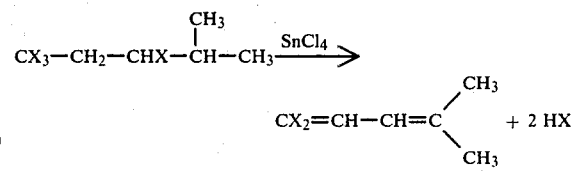

where X is a halogen selected from the group consisting of chlorine, bromine, and fluorine. The four X atoms in the molecule on the left hand side of the above equation may all be the same halogen, or may comprise a combination of two different halogens selected from the above group. A typical example of such a molecule combining two different halogens is 1,1,1-trichloro-3-bromo-4-methylpentane. The result upon cracking this molecule is 1,1-dichloro-4-methyl-1,3-pentadiene plus one mole each of HCl and HBr. The preferred halogen, for reasons of utility of the final product, is chlorine. Thus, the preferred reactant in the above equation is 1,1,1,3-tetrachloro-4-methylpentane. Another example of a reactant with two different halogens is 1,1-difluoro-1,3-dibromo-4-methylpentane.

The term "catalytic amount" is used herein to denote any amount of stannic chloride which will enhance the progress of the reaction. Reasonable reaction rates are normally achieved when the stannic chloride concentration is between about 0.25% and about 10.0% by weight with respect to the 1,1,1,3-tetrahalo-4-methylpentane. The preferred range is between about 0.5% and about 5.0% by weight.

Although the reaction temperature is not an essential aspect of the invention, the temperature chosen will be limited by practical considerations readily apparent to the skilled practitioner. Considerations of economy in terms of heat input and overall reaction time will dictate the lower temperature limit, while the boiling points of the components will dictate the upper temperature limit. The latter can be varied by adjustments in the system pressure. In particular, superatmospheric pressures will allow liquid phase operation at higher temperatures. The result will be an increased reaction rate. In general, it will be most convenient to operate the reaction at a temperature between about 120° C. and about 200° C., preferably between about 140° C. and about 170° C. Since both the initial compound, the catalyst and the desired end product, are in the liquid phase, the reaction will proceed most effectively when the system is under reflux. The hydrogen halide by-product leaves the system as a gas, the evolution of which causes the volatilization and subsequent removal from the system of some of the catalyst, thus necessitating the use of a large initial quantity of catalyst in the reaction mixture. The amount of catalyst lost in this manner can be reduced by operating the system at superatmospheric pressures, for example, up to 25 psig. As mentioned above, the higher pressure will have the further advantage of increasing the reaction rate of the refluxing system.

The presence of air in the system will be detrimental to the purity of the final product, since air will form peroxides with the resulting diene, which will in turn lead to polymerization. During the cracking process, however, the evolution of the hydrogen halide gas serves to sweep the air out the system, and thus prevent the formation of the harmful peroxides. After the cracking process is completed, it will be advantageous to add a stabilizer to the system to prevent polymerization. This purpose can be served by any of the known stabilizing agents such as t-butyl catechol and Ionol® (an antioxidant defined as a trisubstituted phenol—product of Shell Chemical Company).

At the completion of the reaction, the product can be recovered from the reaction mixture by any of the conventional liquid recovery techniques. Additionally, the stannic chloride remaining in the system can be distilled off and retained for reuse. The most useful recovery techniques will be vacuum distillation followed by steam distillation. The latter is particularly useful for the separation of the desired diene from any polymer formed during the reaction.

The advantage of the stannic chloride catalyst over other known catalysts is that it enhances the progress of the reaction with a minimum amount of polymerization. Yields on the order of 85 to 95% are readily obtainable with stannic chloride but are lowered by polymerization of the product during or subsequent to the reaction. The yield will be the highest when polymerization is suppressed in the manner indicated above.

The 1,1,1,3-tetrahalo-4-methylpentane referred to in the reaction above can be prepared by any technique known in the art. One method of preparation is the addition reaction of a tetrahalo methane to 3-methyl-1-butene. Where the four halogens in the resulting substituted pentane are identical, the halogens in the tetrahalomethane are likewise identical and comprise the same four that exist in the product. The preferred tetrahalomethane is carbon tetrachloride. The addition reaction can also be run with a tetrahalomethane which contains two different types of halogen. Examples of the latter are $CCl_3Br$ and $CF_2Br_2$. In the former case, the resulting substituted pentane is 1,1,1-trichloro-3-bromo-4-methylpentane. In the latter 1,1-dichloro-1,3-difluoro-4-methylpentane will result. Either of these substituted pentanes can be used in the cracking reaction described above. A variety of catalysts are known in the art for use in the above described addition reaction. Among these are cupric chloride, cuprous chloride, ferric chloride, ferrous chloride, ferrous chloride with benzoin, ruthenium(II)-triphenylphosphine complexes, organic peroxides, and cobaltous salts. Examples of ruthenium(II)-triphenylphosphine complexes are dichlorotris(triphenylphosphine)ruthenium(II) and dichlorotetrakis(triphenylphosphine)ruthenium(II).

The organic peroxides (including hydrogen peroxide) are defined by the formula R—O—O—R' wherein R and R' are hydrogen or organic radicals. These include the hydroperoxides, where R is hydrogen and R' is alkyl, cycloalkyl, cycloalkenyl, alkaryl, aralkyl, and heterocyclic of up to 12 carbon atoms; the dialkyl peroxides, where R and R' are each alkyl of up to 12 carbon atoms; the diaralkyl peroxides, where R and R' are each aralkyl of up to 20 carbon atoms; the aliphatic peroxy acids where R is hydrogen and R' is alkanoyl or aroyl of up to 12 carbon atoms; the peroxy esters of said peroxy acids, where R is alkyl or aryl of up to 12 carbon atoms and R' is alkanoyl or aroyl of up to 12 carbon atoms; the diacyl peroxides, where R and R' each are alkanoyl of up to 12 carbon atoms; the diaroyl peroxides, where R and R' each are aroyl of up to 12 carbon atoms as well as the dialkyl peroxydicarbonates, 1-hydroxyalkyl hydroperoxides, bis(1-hydroxyalkyl)-peroxides, polyalkylidene peroxides, alkyl 1-hydroalkyl peroxides and peroxy acetals.

Preferred organic peroxides are those wherein R and R' are hydrogen, alkyl of 1–4 carbon atoms, aralkyl of up to 12 carbon atoms, alkanoyl of up to 12 carbon atoms, or aroyl of up to 12 carbon atoms.

Any cobaltous salt soluble in the tetrahalomethane used will be suitable in the addition reaction. Such salts include cobaltous hexamine naphthalene $\beta$-sulfonate, cobaltous hexamine picrate, and the various cobaltous alkylated-naphthalene sulfonates, for example, cobaltous methyl naphthalenesulfonate and cobaltous ethyl naphthalenesulfonate.

The following examples are offered to illustrate the process of the invention, and are not intended to impose limitations thereon.

EXAMPLE I

A 12-ounce aerosol compatibility tube was charged with the following:

| | |
|---|---|
| 175 ml (1.75 moles) | $CCl_4$ |
| 0.2002 g | dichlorotris(triphenyl-phosphine)ruthenium(II) |
| 105 g (1.5 moles) | 3-methylbutene |

The air in the tube was displaced and the tube was placed in a bath at 75° C. for 20 hours with stirring. The tube and contents were then cooled, and the unreacted $CCl_4$ and 3-methylbutene were removed by distillation, leaving 286 g (85% yield) of 1,1,1,3-tetrachloro-4-methylpentane, with 96% purity.

A stirred reaction flask with reflux condenser was charged with 508 g (400 ml, about 2.3 moles) of 1,1,1,3-tetrachloro-4-methylpentane prepared by the above procedure, and 10 ml of $SnCl_4$. The system was heated to reflux for four hours. Of the starting material, 5% remained uncracked. Steam distillation of the product yielded 310 g (88% yield) of 1,1-dichloro-4-methyl-1,3-pentadiene, with an assay by chromatography of 97%.

EXAMPLE II

A 2-liter reactor was charged with 1288 g (1 liter, 5.75 moles) of 1,1,1,3-tetrachloro-4-methylpentane, prepared in a manner similar to that described in Example I, and 25 ml $SnCl_4$. The system was refluxed at 170° C. During reflux, gas chromatography analyses provided the following data:

| Reaction Time | % Cracked |
|---|---|
| 1¼ hours | 29 |
| 3¼ hours | 65 |
| 5¼ hours | 85.5 |
| 6¼ hours | 90 |

The product was vacuum distilled to yield 758 g of the diene in the distillate. To the residue was added 150 ml concentrated HCl diluted with water to 400 ml. The residue was then steam distilled to yield an additional 61 g of the diene, to make a total of 819 g (94% yield), identity confirmed by gas chromatographic analysis.

EXAMPLE III

This example illustrates the results achieved when ferric chloride rather than stannic chloride is used as the cracking catalyst. The advantages of the stannic chloride process are apparent from the data below.

A 500 ml reactor equipped with stirrer and condenser was charged with 200 ml (256 g, 1.14 moles) of 1,1,1,3-tetrachloro-4-methylpentane, and 10 g of $FeCl_3$. The mixture was heated to reflux at about 160° C. After about 1 hour, the reaction mixture formed a thick gel. A solution of 40 ml concentrated HCl diluted to 100 ml with distilled water was added to the gel, and the mixture was steam distilled. Of a possible 170 g (theoretical amount), only 111 g of unpolymerized material was recovered. Of this amount, 47.5% was the uncracked starting material, and 34.4% was the desired product. Conversion was 66%, with a yield of 35%.

What is claimed is:

1. A process for the manufacture of a 1,1-dichloro-4-methyl-1,3-pentadiene which comprises contacting a 1,1,1,3-tetrachloro-4-methylpentane in the liquid phase with a catalytic amount of liquid stannic chloride at a temperature between about 120° C. and about 200° C., and recovering the product therefrom.

2. The process of claim 1 in which the system temperature is between about 140° C. and about 170° C.

3. The process of claim 1 in which the process occurs while the system is under reflux.

4. The process of claim 1 in which the amount of stannic chloride is between about 0.25% and about 10% by weight with respect to the 1,1,1,3-tetrachloro-4-methylpentane.

5. The process of claim 4 in which the amount of stannic chloride is between about 0.5% and about 5% by weight with respect to the 1,1,1,3-tetrachloro-4-methylpentane.

6. The process of claim 1 in which the system is under reflux and the amount of stannic chloride is between about 0.5% and about 5% by weight with respect to the 1,1,1,3-tetrachloro-4-methylpentane.

7. The process of claim 1 in which the 1,1,1,3-tetrachloro-4-methylpentane is prepared by the addition of carbon tetrachloride to 3-methyl-1-butene in the presence of a catalytic amount of a catalyst selected from the group consisting of metallic iron, cupric chloride, cuprous chloride, ferric chloride, ferrous chloride, ferrous chloride with benzoin, ruthenium(II)-triphenylphosphine complexes, organic peroxides and cobaltous salts.

* * * * *